United States Patent [19]

Karny et al.

[11] Patent Number: 4,830,462

[45] Date of Patent: May 16, 1989

[54] OPTICAL-FIBER TYPE POWER TRANSMISSION DEVICE

[75] Inventors: Ziv Karny, Shmariyahu; Rami Arieli, Tel-Aviv; Alan Schwebel, Rehovot, all of Israel

[73] Assignee: Laser Industries Ltd., Tel Aviv, Israel

[21] Appl. No.: 136,620

[22] Filed: Dec. 22, 1987

[30] Foreign Application Priority Data

Apr. 10, 1987 [IL] Israel ........................................ 82163

[51] Int. Cl.⁴ .............................................. G02B 6/10
[52] U.S. Cl. ................................ 350/96.30; 350/96.32
[58] Field of Search ............... 350/96.20, 96.29, 96.30, 350/96.32

[56] References Cited

U.S. PATENT DOCUMENTS 4,389,091  6/1983  Lidholt ............................. 350/96.20
4,607,911  8/1986  Rhodes ............................. 350/96.20
4,726,647  2/1988  Kakii et al. ....................... 350/96.20

Primary Examiner—William L. Sikes
Assistant Examiner—Robert E. Wise
Attorney, Agent, or Firm—Benjamin J. Barish

[57] ABSTRACT

An optical-fiber type power transmission device, comprises an optical fiber for transmitting the power from a power input end through a power output end of the optical fiber; an opaque protective sleeve over the optical fiber and having an inner diameter larger than the outer diameter of the optical fiber to define a gas passageway therebetween; and a tubular waveguide secured to the protective sleeve at the power output end of the optical fiber and projecting past the power output end. The tubular waveguide is unattached to the optical fiber to permit the fiber to move with respect to the tubular waveguide and protective sleeve during the bending of the device.

20 Claims, 1 Drawing Sheet

OPTICAL-FIBER TYPE POWER TRANSMISSION DEVICE

BACKGROUND OF THE INVENTION

The present invention relates to optical-fiber type power transmission devices. The invention is particularly useful in infrared optical fibers for transmitting power in the order of 1-100 watts, e.g., for laser surgery; and the invention is therefore described below with respect to this application.

Optical fibers of the low-power type used for communication purposes are provided with an external cladding for purposes of protecting the fiber and also for purposes of decreasing the numerical aperture of the fiber, i.e., the divergence angle of the energy exiting from the fiber. It is also known to apply a metal ferrule or sleeve to the outer end of the optical fiber to protect it, and also to enable attachment of an accessory. Such ferrules are usually attached to the clad of the fiber end by mechanical means, e.g., by swaging or pinching the ferrule onto the fiber end.

However, such metal ferrules cannot be applied to unclad optical fibers used for transmitting power.

Thus, the ferrule if applied to uncladded fiber will absorb energy energizing from it unless the ferrule is of a transparent material suitable for that wavelength. Additional difficulties arise when using silver halide infrared transmitting fibers because of their high chemical reactivity.

Further, most of the power transmitting fibers have an external jacket to the fiber for gas cooling. Such an assembly attached with a ferrule would have drawbacks especially when used as a laser scalpel because of the difficult elongation of the jacket and fiber which could result during the manipulation of the assembly.

In addition, when using uncladded fiber having a large numerical aperature (i.e., a large divergence angle of the energy leaving the fiber tip), the distance from the fiber tip to the protruding protective ferrule must be kept at a minimum so that the highly divergent beam does not impinge on the ferrule. Further, the protective feature of the ferrule on the tip is effectively lost, especially in laser surgery procedure, where there is much debris, etc.

An object of the present invention is to provide an optical-fiber type power transmission device having advantages in the above respects.

BRIEF SUMMARY OF THE INVENTION

According to the present invention, there is provided an optical-fiber type power transmission device comprising an optical fiber for transmitting the power from a power input end through a power output end of the optical fiber; an opaque protective sleeve over the optical fiber and having an inner diameter larger than the outer diameter of the optical fiber to define a gas passageway therebetween; and a tubular waveguide extending between the optical fiber and the protective sleeve at the power output end of the optical fiber and projecting past the power output end. The tubular waveguide is unattached to the optical fiber to permit the fiber to move with respect to the tubular waveguide and protective sleeve during the bending of the device.

Such a construction provides a number of important advantages which are particularly important when used with infrared optical fibers for transmitting power in laser surgery. Thus, the waveguide at the power output end of the optical fiber decreases the numerical aperture of the fiber, i.e., the divergence angle of the outputted power. This increases the power density applied to the tissue receiving the laser energy, decreases the sensitivity of the working tip to the tissue to receive the laser energy, and permits larger working distances between the tip and the tissue. In addition, the waveguide also protects the sensitive fiber tip; preferably the waveguide is dimensioned such that it projects past the fiber tip during all manipulations of the device. Further, by circulating a gas through the gas passsageway between the optical fiber and the protective sleeve and through the waveguide, (the waveguide thereby acting also as a nozzle), the heat build-up at the sensitive fiber tip is minimized, the fiber tip is maintained clean of contamination, and also the working area in front of the fiber tip is maintained free of smoke and other contamination.

Still further, since the waveguide at the end is unattached to the optical fiber, the corrosion problem is substantially eliminated, and moreover the fiber end can be bent without producing stresses in the fiber since the fiber is free to move with respect to both the waveguide and the protective sleeve. Still further, the arrangement permits the construction of power transmission devices of very small diameter, as low as 2-3 mm, enable use of the device in endoscopes and catheters, for applying laser energy directly against selected tissue in body cavities or blood vessels.

Several embodiments of the invention are described below for purposes of example.

In one described embodiment, the tubular waveguide is secured directly to the protective sleeve at the power output end of the optical fiber and has an inner diameter larger than the outer diameter of the optical fiber to provide a gas passageway therebetween.

Two further embodiments of the invention are described below wherein the waveguide is secured indirectly to the protective sleeve, i.e., the waveguide is secured to a tubular housing overlying the output end of the optical fiber which housing is secured to the protective sleeve. The inner diameter of the housing is larger than the outer diameter of the optical fiber at the output end to provide a gas passageway therebetween. In addition, the device further includes an optical window at the power output end of the optical fiber and secured between the waveguide and housing at the juncture thereof, which juncture is provided with recesses to define a gas passageway from one side of the optical window to the opposite side thereof. Such a construction, including a window, even further protects the sensitive fiber tip, which is particularly important when the device is used in laser surgery.

Further features and advantages of the invention will be apparent from the description described below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
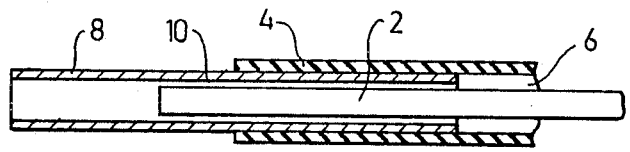
FIG. 1 is a longitudinal sectional view illustrating one embodiment of the invention.

FIG. 1 illustrates the power output end of an optical fiber 2 of the infrared type, for example of silver chloride or silver bromide crystal material. The optical fiber 2 is provided with an opaque protective sleeve 4 extending for substantially the complete length of the optical fiber from its input end (not shown) to the illustrated output end, the sleeve 4 terminating slightly short of the power output end as shown in FIG. 1. The opaque protective sleeve 4 has an inner diameter larger than the outer diameter of the optical fiber 2 so as to define a gas passageway 6 therebetween.

A tubular waveguide 8 extends between the optical fiber 2 and the protective sleeve 4 at the power output end of the optical fiber 2 and projects past that end of the optical fiber sufficiently so as to protect the fiber tip under all conditions of bending the device. The tubular waveguide 8 has an outer diameter equal to the inner diameter of the opaque protective sleeve 4 and is secured thereto, as by adhesive bonding. The inner diameter of the tubular waveguide 8, however, is larger than the outer diameter of the optical fiber 2 so as to provide a gas passageway 10 therebetween communicating with gas passageway 6 between the optical fiber and the opaque protective sleeve 2.

Waveguide 8 is preferably in the form of a ceramic tube which is non-reactive with respect to the silver chloride or silver bromide crystal material of optical fiber 2. Another alternative would be to make waveguide 8 of a metal tube, such as stainless steel, having an inner coating of gold which is also non-reactive with respect to the material of the optical fiber 2.

The opaque protective sleeve 4 is preferably polytetraflourethyene. However, it could also be another suitable opaque material such as of polyethylene or nylon.

It will be seen that the waveguide 8 projecting past the power output end of the optical fiber 2, minimizes the numerical aperture and thus reduces the divergence angle of the power outputted from the fiber. As mentioned earlier, this enables the waveguide not only to protect the sensitive tip of the optical fiber 2, but also to concentrate the outputted energy to increase the power density, and to shape the beam applied to the tissue receiving the energy. In addition, this arrangement permits a larger working distance between the fiber tip and the tissue receiving the energy, and also decreases the dependence of the power received by the tissue to the distance between the tissue and the output tip. All the above advantages are particularly important when the device is used in laser surgery.

It will thus be seen that tube 8 acts not only as a waveguide for directing the optical energy to the output end of the device, but also acts as a nozzle for directing the gas flowing through passageways 6 and 10. This gas serves to dissipate the heat generated at the output end of the device, to maintain the fiber tip free of contamination, and also to remove the smoke, etc., from the working area thereby enabling the surgeon better to view the working area.

Figure 2:
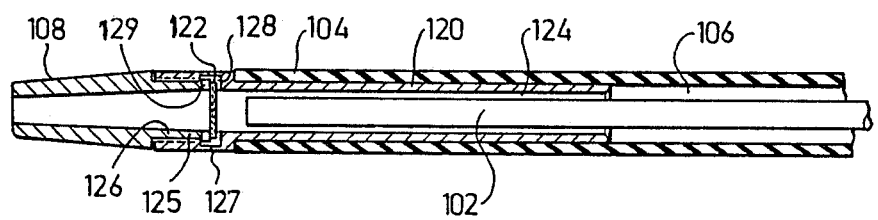
FIG. 2 is a longitudinal sectional view illustrating a second embodiment of the invention.

FIG. 2 illustrates another construction that may be used at the power output tip of the optical fiber, therein designated 102. The construction illustrated in FIG. 2 also includes an opaque protective sleeve 104 over the optical fiber, and a waveguide (nozzle) 108 secured to the optical sleeve 104 at the power output end of the optical fiber and projecting past the power output end. In this case, however, waveguide 108 is not secured directly to the opaque protective sleeve 104, but rather is secured to a housing 120 which is in turn secured to the protective sleeve. In addition, the construction illustrated in FIG. 2 further includes an optical window 122 at the power output end of the optical fiber 102 and secured at the juncture between the waveguide 108 and housing 120.

As shown in FIG. 2, housing 120 has an inner diameter larger than the outer diameter of the optical fiber 102 so as to provide a gas passageway 124 between the optical fiber and the housing. This passageway communicates with gas passageway 106 between the optical fiber and the opaque protective sleeve 104. Housing 120 is enlarged in diameter just forwardly of the output end of optical fiber 102 and is formed with a tubular socket 125 forwardly of the output end of the fiber receiving a tubular stem 126 formed at the end of waveguide 108. Any suitable means may be used for securing the waveguide in socket 125 of housing 120, for example by a press fit, swaging, or adhesive. Optical window 122 is secured between the tip of stem 126 and the end of socket 125 so as to be spaced slightly forwardly of the output end of the optical fiber 102.

As shown in FIG. 2, the end of socket 125 is formed with an annular recess 127 so as to overlie both sides of window 122. At one side of window 122, socket 125 is formed with a plurality of radially-extending openings 128; and at the opposite side of the window, stem 126 of waveguide 108 is likewise formed with a plurality of radially-extending openings 129. Recess 127 and openings 128, 129 thus define a plurality of gas passsageways from one side of optical window 122 to the opposite side for the gas applied to passageways 106 and 124. The gas circulating through these passageways prevents build up of heat at the optical window in the output end of the optical fiber 102, dissipates the heat from this region, and clears the working area of smoke, etc.

The inner diameter of waveguide (nozzle) 108 is preferably tapered in the construction illustrated in FIG. 2, decreasing in diameter towards the output end. This further decreases the divergence spot size at the exit from the nozzle, and increases the power density of the beam applied to the tissue.

Figure 3:
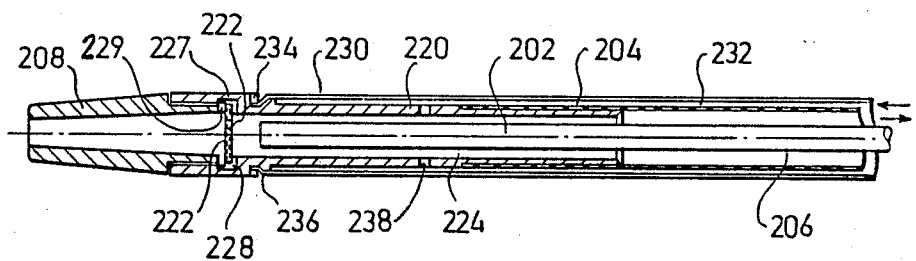
FIG. 3 is a longitudinal sectional view illustrating a third embodiment of the invention.

FIG. 3 illustrates a construction similar to that of FIG. 2, including an optical fiber 202, an opaque protective sleeve 204, a waveguide (nozzle) 208, a housing 220, an optical window 222, and air passageways defined by annular recess 227 and radial openings 228, 229 around the optical window so as to permit gas flow from one side to the opposite side of the window. In the construction illustrated in FIG. 3, however, the opaque protective sleeve 204 is an inner protective sleeve, the construction also including an outer protective sleeve, therein designated 230. The outer protective sleeve 230 has an inner diameter larger than the outer diameter of the inner protective sleeve 204 so as to define an air passageway 232 between the two sleeves.

The outer protective sleeve 230 is attached to housing 222 by means of a clamp 234 applied over the end of sleeve 230 and secured to a rib 236 formed in the outer face of housing 220 substantially in alignment with the output end of the optical fiber 202. Housing 220 is extended inwardly towards the input end of the optical fiber, and the inner protective sleeve 232 is secured to this inner end of the housing by any suitable means, such as by an adhesive. Housing 220 is further formed with a plurality of openings 238 connecting gas passageway 232 between the outer sleeve 230 and the inner sleeve 204, and gas passageway 224 between the housing and the optical fiber.

In the construction illustrated in FIG. 3, when gas is applied to passageway 232 between the two sleeves 204 and 230, the gas passes through openings 238 into passageway 224. Part of the gas circulates across the inner face of the optical window 220 and out through passageway 206 between the inner sleeve 204 and the optical fiber 202; whereas another part of the gas passes through the passageways formed by recess 227 and opening 228, 229 to the opposite side of the optical window and out through the end of waveguide (nozzle) 208. It will thus be seen that the gas circulates across both faces of the optical window 222, thereby maintaining it, as well as the tip of the optical fiber 202 and the working area in front of it, free of contamination, while also preventing a build up of heat in this region.

While the invention has been described with respect to three preferred embodiments, it will be appreciated that many other variations, modifications and applications of the invention may be made.

What is claimed is:

1. An optical-fiber type power transmission device, comprising:
   an optical fiber for transmitting the power from a power input end through a power output end of the optical fiber;
   an opaque protective sleeve over the optical fiber and having an inner diameter larger than the outer diameter of the optical fiber to define a gas passageway therebetween;
   and a tubular waveguide extending between said optical fiber and protective sleeve at the power output end of the optical fiber and projecting past said power output end, said tubular waveguide being unattached to said optical fiber to permit said fiber to move with respect to said tubular waveguide and protective sleeve during the bending of the device.

2. The device according to claim 1, wherein said tubular waveguide is secured directly to the protective sleeve at the power output end of the optical fiber and has an inner diameter larger than the outer diameter of the optical fiber to provide a gas passageway therebetween.

3. The device according to claim 1, wherein said tubular waveguide is secured to a tubular housing overlaying the output end of the optical fiber, which housing is secured to said protective sleeve; the inner diameter of the housing being larger than the outer diameter of the optical fiber at said output end to provide a gas passageway therebetween.

4. The device according to claim 3, further including an optical window at the power output end of the optical fiber and secured between said waveguide and housing at the juncture thereof; the juncture of said waveguide and housing being provided with an annular recess overlying said optical window and with radial openings on both sides thereof to define a gas passageway from one side of the optical window to the opposite side thereof.

5. The device according to claim 3, wherein the output end of said housing is secured to said protective sleeve.

6. The device according to claim 5, wherein said protective sleeve is an inner protective sleeve and is secured to the housing at a location between the power output and input ends of the optical fiber; said device further including an outer protective sleeve clamped to an annular rib formed in the housing at the power output end thereof, and spaced from the outer face of the housing to define a gas passageway therebetween; said housing being formed with a gas passageway opening therethrough between said annular rib to which the outer protective sleeve is clamped and the location of the housing at which the inner protective sleeve is secured.

7. The device according to claim 1, wherein said tubular waveguide has a uniform inner diameter.

8. The device according to claim 1, wherein said tubular waveguide has a tapered inner diameter, decreasing towards its power output end.

9. The device according to claim 1, wherein said optical fiber is an infrared fiber of silver chloride or silver bromide crystal material.

10. The device according to claim 1, wherein said protective sleeve is polytetrafluoroethylene, polyethylene, or nylon.

11. The device according to claim 1, wherein said waveguide is a ceramic material.

12. The device according to claim 1, wherein said waveguide is stainless steel coated on its inner face with gold.

13. An optical-fiber type power transmission device, comprising:
    an optical fiber for transmitting the power from a power input end through a power output end of the optical fiber;
    an opaque protective sleeve over the optical fiber and having an inner diameter larger than the outer diameter of the optical fiber to define a gas passageway therebetween;
    and a tubular waveguide extending between said optical fiber and said protective sleeve at the power output end of the optical fiber and projecting past said power output end;
    said tubular waveguide being unattached to said optical fiber to permit said fiber to move with respect to said tubular waveguide and protective sleeve during the bending of the device;
    said tubular waveguide being secured directly to the protective sleeve at the power output end of the optical fiber and having an inner diameter larger than the outer diameter of the optical fiber to provide a gas passageway therebetween.

14. The device according to claim 13, wherein said tubular waveguide is secured to a tubular housing overlying the output end of the optical fiber, which housing is secured to said protective sleeve; the inner diameter of the housing being larger than the outer diameter of the optical fiber at said output end to provide a gas passageway therebetween.

15. The device according to claim 14, further including an optical window at the power output end of the optical fiber and secured between said waveguide and housing at the juncture thereof; the juncture of said waveguide and housing being provided with an annular recess overlying said optical window and with radial openings on both sides thereof to define a gas passageway from one side of the optical window to the opposite side thereof.

16. The device according to claim 14, wherein the output end of said housing is secured to said protective sleeve.

17. The device according to claim 16, wherein said protective sleeve is an inner protective sleeve and is secured to the housing at a location between the power output and input ends of the optical fiber; said device further including an outer protective sleeve clamped to an annular rib formed in the housing at the power output end thereof, and spaced from the outer face of the housing to define a gas passageway therebetween; said housing being formed with a gas passageway opening therethrough between said annular rib to which the outer protective sleeve is clamped and the location of the housing at which the inner protective sleeve is secured.

18. The device according to claim 13, wherein said tubular waveguide has a uniform inner diameter.

19. The device according to claim 13, wherein said tubular waveguide has a tapered inner diameter, decreasing towards its power output end.

20. The device according to claim 13, wherein said optical fiber is an infrared fiber of silver chloride crystal material.

* * * * *